United States Patent [19]

Gschwend et al.

[11] 4,309,349
[45] Jan. 5, 1982

[54] STEREOSPECIFIC PROCESS FOR PREPARING EPOXYBENZODIOXANS

[75] Inventors: Heinz W. Gschwend, New Providence; Charles F. Huebner, Chatham, both of N.J.

[73] Assignee: Ciba-Geigy Corporation, Ardsley, N.Y.

[21] Appl. No.: 193,509

[22] Filed: Oct. 1, 1980

Related U.S. Application Data

[60] Continuation-in-part of Ser. No. 27,705, Apr. 9, 1979, abandoned, which is a continuation of Ser. No. 19,993, Mar. 12, 1979, Pat. No. 4,261,907, which is a division of Ser. No. 873,456, Jan. 30, 1978, abandoned.

[51] Int. Cl.³ .................................... C07D 407/04
[52] U.S. Cl. ..................... 260/340.3; 260/340.5 R; 260/348.49; 568/442
[58] Field of Search .............. 260/340.3, 340.5 R

[56] References Cited

U.S. PATENT DOCUMENTS

2,699,438  1/1955  Bock ........................... 528/361
3,101,345  8/1963  Schmidt ..................... 260/340.3

OTHER PUBLICATIONS

Howe, R., et al., *J. Med. Chem.*, 13(2), 169–176 (1970).

*Primary Examiner*—Richard A. Schwartz
*Attorney, Agent, or Firm*—Norbert Gruenfeld

[57] ABSTRACT

The process depicted, for example, by the formulae

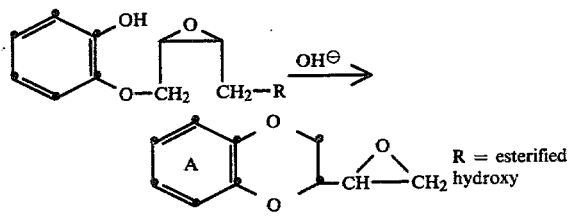

yields valuable intermediates in the manufacture of drugs.

9 Claims, No Drawings

STEREOSPECIFIC PROCESS FOR PREPARING EPOXYBENZODIOXANS

CROSS-REFERENCE TO RELATED APPLICATIONS

This is a continuation-in-part of Ser. No. 027,705, filed Apr. 9, 1979, now abandoned, which is a continuation of Ser. No. 019,993, filed Mar. 12, 1979, now U.S. Pat. No. 4,261,907, which is a divisional of Ser. No. 873,456, filed Jan. 30, 1978, now abandoned.

BACKGROUND OF THE INVENTION

U.S. Pat. Nos. 3,312,592; 3,910,930 and 3,914,238 disclose pharmacologically active 2-(2-amino-1-hydroxyethyl)-1,4-benzodioxans, which are obtained as mixtures of diastereoisomers, separable only by cumbersome methods. According to the present invention a stereospecific process is provided, yielding intermediates for said compounds in the pure erythro or threo forms, and requiring but simple, inexpensive starting materials. Moreover, said process is especially suited for the unambiguous preparation of ring-A-substituted 1,4-benzodioxans.

SUMMARY OF THE DISCLOSURE

The present invention concerns and has for its object the provision of a new stereospecific process for the preparation of 2-(2-substituted-1-hydroxyethyl)-1,4-benzodioxans corresponding to Formula I

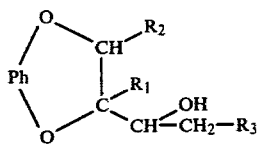

wherein Ph is unsubstituted 1,2-phenylene or 1,2-phenylene substituted by one to three identical or different members selected from lower alkyl; free, etherified or esterified hydroxy, such as lower alkoxy, lower alkylenedioxy, benzyloxy, lower alkanoyloxy or halogeno; trifluoromethyl; or nitro; each of $R_1$ and $R_2$ is hydrogen or lower alkyl and $R_3$ is free or said esterified hydroxy; or a secondary or tertiary amino group, such as mono- or di-lower alkylamino, lower alkyleneimino unsubstituted or substituted in a position separated from the nitrogen atom by at least 2 carbon atoms by one member selected from free, etherified or esterified hydroxy, such as lower alkoxy, lower or higher alkanoyloxy, and/or one member selected from lower alkyl, HPh-lower alkyl, HPh, unsubstituted naphthyl or naphthyl substituted as Ph, unsubstituted furyl, thiophenyl, pyridyl, benzofuryl, benzothiophenyl, quinolyl, isoquinolyl or

or said heterocyclics substituted as Ph; or of therapeutically acceptable acid addition salts thereof; which compounds are either known or new therapeutically useful products, e.g. β-adrenergic blocking or antihypertensive agents, or valuable intermediates thereof.

Said stereospecific process comprises the following steps:

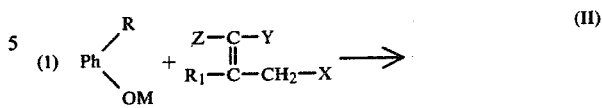

wherein R is CHO or lower alkanoyloxy, M is one equivalent of a metal atom, such as of an alkaline earth or preferably an alkali metal, X is a halogen atom and one of Y and Z is $R_2$ and the other is $CH_2X$;

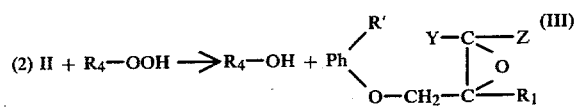

wherein $R_4$ is hydrogen, lower alkanoyl, lower haloalkanoyl, HPhCO, $HOOC-C_2H_4-CO$, or HOOC-Ph-CO and R' is lower alkanoyloxy or formyloxy;

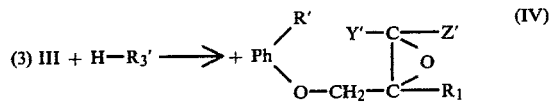

wherein one of Y' and Z' is $R_2$ and the other is $CH_2R_3'$, in which $R_3'$ is selected from $R_3$ but being different from X;

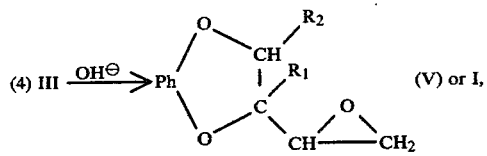

wherein $R_3 = X$;

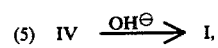

wherein $R_3$ is different from X.

In case Y or Y'=$R_2$ in III (resulting from the trans-olefin), the erythro-compounds are obtained, and if Z or Z'=$R_2$ (resulting from the cis-olefin), the threo-compounds are formed.

The conversion of compounds V into those of Formula I is disclosed in said U.S. Pat. No. 3,914,238 without reference to a stereochemically single entity.

DESCRIPTION OF THE PREFERRED EMBODIMENTS

The 1,2-phenylene group Ph is preferably unsubstituted or monosubstituted, and its substituents illustrated by the following groups; lower alkyl, e.g. methyl, ethyl, n- or i-propyl or -butyl; hydroxy; lower alkoxy, e.g. methoxy, ethoxy, n- or i-propoxy or -butoxy, lower alkylenedioxy, e.g. methylenedioxy, 1,1- or 1,2-ethylenedioxy; benzyloxy; alkanoyloxy with 1-4 carbons, e.g. formyloxy or acetoxy halogeno, e.g. fluoro, chloro or bromo; trifluoromethyl; or nitro.

Each of $R_1$ and $R_2$ is preferably hydrogen, but also lower alkyl, advantageously methyl, or another of those mentioned above.

The substituent $R_3$ is preferably X, especially chloro, but also bromo or iodo; hydroxy or R', e.g. formyloxy, acetoxy, propionyloxy or pivalyloxy. A mono- or di-lower alkylamino group $R_3$ contains preferably secondary or tertiary alkyl groups with 3 to 7 carbon atoms, such as i-propyl, i- or t-butyl, -pentyl or -hexyl, and a lower alkyleneimino group is preferably pyrrolidino, piperidino or hexamethyleneimino, either unsubstituted or preferably substituted in positions 2 or 3 by hydroxy, lower alkoxy or alkanoyloxy, e.g. those mentioned above, or higher alkanoyloxy, e.g. octanoyloxy, decanoyloxy, undecanoyloxy, lauroyloxy, myristoyloxy, palmitoyloxy or stearoyloxy. Said 2 or 3 position preferably carries in addition to hydrogen or said other groups also a lower alkyl group, preferably said secondary or tertiary alkyl groups; a HPh-lower alkyl group, e.g. benzyl, 1- or 2-phenethyl; but preferably a phenyl group HPh as illustrated above; furthermore, 1- or 2-naphthyl optionally substituted as shown for HPh; unsubstituted 2- or 3-furyl or -thiophenyl; 2-, 3- or 4-pyridyl; 2-or 3-(1-benzofuryl or 1-benzothiophenyl); 2- 3- or 4-quinolyl or 1-, 3- or 4-isoquinolyl, or said groups substituted by one to three lower alkyl, preferably methyl groups; or preferably said unsubstituted 2-oxo-1-benzimidazolyl group.

The symbol M represents preferably lithium, sodium or potassium, but also one equivalent of magnesium or calcium, and the hydroxy ion in step 4 is preferably provided from a strong base, such as an alkali metal hydroxide, e.g. potassium hydroxide, or a strong quaternary nitrogen base, such as a lower trialkylbenzylammonium hydroxide.

In case step 2 is carried out with a compound II, wherein R is lower alkanoyloxy, the epoxidizing agent $R_4OOH$ may be hydrogen peroxide in the presence of an organic nitrile, preferably a HPh-CN, such as benzonitrile. In case R is CHO, both the Baeyer-Villiger reaction and epoxidation consume one mole equivalent of one of said peracids each, such as peracetic, pertrifluoroacetic, perbenzoic, 3-chloroperbenzoic, persuccinic or monoperphthalic acid. Depending on the use of the cis- or transolefins, the stereospecific course of this process is guaranteed.

The above-mentioned reaction steps are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure. Thus, for example, the condensation steps 1 and 4 are preferably carried out in an aqueous medium, which may contain phase-transfer agents, such as tetra-lower alkylammonium hydroxides, e.g. tetrabutylammonium hydroxide, or crown-ethers, and/or lower alkanols, e.g. methanol, ethanol or isopropanol. If said water-miscible solvents are replaced in step 4 by water-immiscible solvents, such as aliphatic ethers or halides, e.g. diethyl ether or methylene chloride, or hydrocarbons, e.g. cyclohexane or benzene, the condensation can be stopped at the preceding halohydrin stage.

The peroxidation should be carried out in low boiling haloalkanes, e.g. methylene chloride for said aromatic peracids; lower alkyl alkanoates, e.g. ethyl acetate, for aliphatic peracids; dimethylformamide for succinoyl peroxide; and benzonitrile with an alkali metal bicarbonate, e.g. potassium bicarbonate, for hydrogen peroxide. Said bicarbonates or carbonates may also be used with pertrifluoroacetic acid, which destroy any excess of the peracid after the olefin has been consumed.

The optional condensation step 3 is advantageously carried out in an excess of the amine $HR_3'$ only, or in the presence of a di-lower alkylformamide, e.g. dimethylformamide.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in different sequence, or they are used in the form of their salts or optically pure antipodes. Thus for example, step 1 may also be carried out with the free bisphenole and the epoxide of the olefin, to yield compounds III, with R' being also hydroxy, directly. Said phenols III or IV can also be obtained by reacting the formates III or IV first with a hydrolyzing agent other than said bases, such as a tri-lower alkylamide, e.g. triethylamine, whereupon the ring-closure to the dioxans V or I is achieved with said inorganic or ammonium bases. Mainly those starting materials would be used in said reactions, that lead to the formation of those compounds indicated above as being especially valuable, e.g. those mentioned in said patents.

Said compounds so obtained can be converted into each other according to known methods. Thus, for example, compounds of Formula I with $R_3=X$ can be reacted with $HR_3'$ analogous to step 3, advantageously in a lower alkanol, e.g. ethanol or isopropanol, or said other diluents; or with an aqueous base, e.g. an alkali metal hydroxide or carbonate, in order to obtain the glycols with $R_3=OH$. Moreover, in compounds of Formula II or III any group $CH_2X$ can either be converted into another such group, e.g. chloromethyl into bromo- or iodomethyl, or into another esterified hydroxymethyl group, such as lower alkanoyloxymethyl, e.g. acetoxymethyl, the latter advantageously in compounds II. This can be achieved by reacting said compounds II or III with an alkali metal lower alkanoate or halide respectively, e.g. sodium acetate, bromide or iodide, in order to facilitate either epoxidation, or amination with $HR_3'$. Compounds of Formula V can be re-converted into the halohydrins I with $R_3=X$, by reaction with a hydrogen halide, e.g. hydrogen bromide, in an inert solvent, preferably a halogenated aliphatic, hydrocarbon, such as methylene chloride.

Finally, the compounds of Formula I are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide, basic salt or cation exchange preparation, e.g. an alkali metal hydroxide or carbonate. Said acid accition salts are preferably such of therapeutically acceptable inorganic or organic acids, such as strong metalloidic acids, for example hydrohalic, e.g. hydrochloric, hydrobromic or hydriodic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid. These or other salts, for example, the picrates, can also be used for purification of the base obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

The new compounds of the invention are those of Formula III and IV, wherein Ph is preferably 1,2-phenylene unsubstituted or monosubstituted by hydroxy, benzyloxy, fluoro, chloro, bromo, trifluoromethyl, nitro, alkyl, alkoxy or alkanoyloxy with 1–4 carbons or alkylenedioxy with 1 to 2 carbons, R' is hydroxy or alkanoyloxy with 1–4 carbons, one of Y and Z is $R_2$ and the other is (chloro, bromo, iodo, $C_1$–$C_4$-alkanesulfonyloxy or alkanoyloxy)-methyl, and each of $R_1$ and $R_2$ is hydrogen or methyl; or one of Y' and Z' is $R_2$ and the other is $CH_2$-$R_3'$ in which $R_3'$ is mono-alkylamino containing secondary or tertiary alkyl groups with 3 to 7 carbon atoms, or lower alkyleneimino unsubstituted or substituted in positions 2 or 3 by hydroxy, lower alkoxy, lower alkanoyloxy, higher alkanoyloxy, and/or said secondary or tertiary alkyl, HPh-lower alkyl, HPh, 1- or 2-naphthyl optionally substituted as shown for HPh; unsubstituted 2- or 3-furyl or -thiophenyl; 2-, 3- or 4-pyridyl; 2- or 3-(1-benzofuryl or 1-benzothiophenyl); 2-, 3- or 4-quinolyl, 1-, 3- or 4-isoquinolyl, or 2-oxo-1-benzimidazolyl or said heterocyclics substituted by 1 to 3 lower alkyls; or an acid addition salt thereof.

More preferred are said compounds III and IV, wherein Ph is 1,2-phenylene unsubstituted or monosubstituted by methyl, methoxy, methylenedioxy, benzyloxy, formyloxy, acetoxy, fluoro, chloro, trifluoromethyl or nitro, R' is hydroxy, formyloxy or acetoxy, one of Y and Z is hydrogen and the other is chloromethyl, bromomethyl, iodomethyl, acetoxymethyl or mesyloxymethyl and $R_1$ is hydrogen; or one of Y' and Z' is hydrogen and the other is CH-$R_3'$ in which $R_3'$ is i-propylamino, i- or t-butylamino, -pentylamino or -hexylamino; pyrrolidino, piperidino or hexamethyleneimino unsubstituted or substituted in positions 2 or 3 by hydroxy, $C_1$–$C_4$ alkoxy or $C_1$–$C_{18}$-alkanoyloxy and HPh or 1-$R_1$-2-oxo-1-benzimidazolyl, or an acid addition salt thereof.

Most preferred are compounds of Formulae III and IV, wherein Ph is 1,2-phenylene, 3-methoxy-1,2-phenylene or 5-chloro-1,2-phenylene, R' is formyloxy, one of Y and Z is hydrogen and the other is chloromethyl, iodomethyl acetoxymethyl or mesyloxymethyl and $R_1$ is hydrogen; or one of Y' and Z' is $R_2$ and the other is $CH_2$-$R_3'$ in which $R_3'$ is t-butylamino, 4-hydroxy-4-phenylpiperidino or 2-oxo-1-benzimidazolyl, or an acid addition salt thereof.

EXAMPLE 1

To 1.2 lt of refluxing water, 1 ml of 40% aqueous tetrabutylammonium hydroxide, 125 ml of salicylaldehyde and 150 ml of cis-1,4-dichloro-2-butene are added while vigorously stirring, followed by the dropwise addition of the solution of 42 g of sodium hydroxide in 200 ml of water at such a rate that the pH of the mixture is kept between 7 and 8. Thereafter the mixture is refluxed until the pH is about 7, cooled and extracted with methylene chloride. The extract is washed with 5% aqueous sodium hydroxide, dried, evaporated, the residue distilled and the fraction boiling at 137°–140°/0.1 mmHg collected, to yield the 2-(4-chloro-cis-2-butenyloxy)-benzaldehyde.

To the solution of 24 g thereof in 500 ml of methylene chloride 0.2 g of 2,4,6-tributylphenol and 55 g of 85% 3-chloroperbenzoic acid are added and the mixture is refluxed for 3 days. It is cooled, filtered and the filtrate washed with 5% aqueous sodium sulfite and 5% aqueous sodium bicarbonate, dried and evaporated, to yield the 2-(4-chloro-cis-2,3-epoxybutyloxy)-phenyl formate, showing NMR-peaks at 3.4, 3.6, 4.2, 6.9 and 8.25 ppm.

To the solution of 4.6 g thereof in 24 ml of methanol is added dropwise 24 ml of 10% aqueous potassium hydroxide while stirring under nitrogen and maintaining the temperature below 30°. After stirring for 18 hours at room temperature the mixture is partly evaporated, the residue taken up in water and the mixture extracted with diethyl ether. The extract is washed with water, dried evaporated, the residue distilled and the fraction boiling at 120°/0.2 mmHg collected, to yield the d,ρ-threo- or (R-S)(S-R)-2-oxiranyl-1,4-benzodioxan of the formula

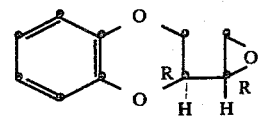

EXAMPLE 2

Replacing in Example 1 the cis-1,4-dichloro-2-butene by the same amount of trans-1,4-dichloro-2-butene and following the procedure as described in said example, the 2-(4-chloro-trans-2-butenyloxy)-benzaldehyde is obtained, boiling at 147°–148°/0.15 mmHg (mentioned in German Pat. No. 1,926,023 without details as to preparation).

24 g thereof are oxidized as described previously, to yield the 2-(4-chloro-trans-2,3-epoxybutyloxy)-phenyl formate, showing NMR-peaks at 3.2, 3.5, 4.1, 7.0 and 8.2 ppm.

4.6 g thereof are ring-closed as illustrated by Example 1, to yield the d,ρ-erythro- or (R-R)(S-S)-2-oxiranyl-1,4-benzodioxan of the formula

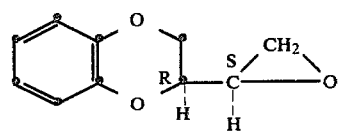

boiling at 120°/0.2 mmHg. The product crystallizes m.p. 45°.

EXAMPLE 3

To the solution of 6 g of sodium iodide in 150 ml of acetone 5 g of 2-(4-chloro-cis-2,3-epoxybutyloxy)-phenyl formate are added and the mixture stirred for 24 hours at room temperature in the dark. It is filtered, the filtrate evaporated and the residue taken up in water. The mixture is extracted with methylene chloride, the extract dried and evaporated, to yield the 2-(4-iodo-cis-2,3-epoxybutyloxy)-phenol formate.

It is dissolved in 25 ml of dimethylformamide and 3.5 g of 4-hydroxy-4-phenylpiperidine are added while stirring, followed by 5 ml of triethylamine. The mixture is stirred at 25° for 2 days in the dark, diluted with water, filtered and the residue washed with water, to yield the 2-[4-(4-hydroxy-4-phenylpiperidino)-cis-2,3-epoxybutyloxy]-phenyl formate.

The solution of 3 g thereof in 12 ml of methanol is added dropwise to 12 ml of 10% aqueous potassium hydroxide while stirring under nitrogen and maintaining the temperature below 30°. After stirring for 18 hours at room temperature the mixture is evaporated, the residue taken up in water and the mixture extracted with diethyl ether. The extract is washed with water, dried and evaporated. The residue is recrystallized from isopropanol, to yield the d,p-threo-2-[2-(4-hydroxy-4-phenylpiperidino)-1-hydroxyethyl]-benzodioxan melting at 116°–118°.

EXAMPLE 4

The mixture of 3 g of d,p-erythro-2-oxiranyl-1,4-benzodioxan, 1.9 g of 4hydroxy-4-phenylpiperidine and 20 ml of isopropanol is refluxed for 7 hours. After cooling to room temperature 0.7 ml of methanesulfonic acid are added while stirring and the mixture is allowed to stand in the refrigerator overnight, to yield the d,p-erythro-2-[2-(4-hydroxy-4-phenylpiperidino)-1-hydroxyethyl]-1,4-benzodioxan methanesulfonate, melting after recrystallization from aqueous isopropanol-diethyl ether at 212°–213°.

1 g thereof is suspended in 20 ml of water, the mixture made basic with aqueous sodium hydroxide and extracted with methylene chloride. The extract is dried, evaporated and the residue recyrstallized from isopropanol, to yield the corresponding free base melting at 118°. It is identical with that disclosed in U.S. Pat. No. 3,914,238.

EXAMPLE 5

The mixture of 3 g of d,p-threo-2-oxiranyl-1,4-benzodioxan and 20 ml of tert. butylamine is heated in a sealed tube to 100° for 10 hours and then evaporated. The residue is taken up in aqueous ammonia, the mixture extracted with chloroform, the extract dried, evaporated and the residue recrystallized from petroleum ether, to yield the d,p-threo-2-(2-tert. butylamino-1-hydroxyethyl)-benzodioxan melting at 84°–85°.

It is dissolved in the minimum amount of ethanol, the solution acidified with etanolic hydrogen chloride and diluted with diethyl ether, to yield the corresponding hydrochloride, melting at 192–194 after recrystallization from ethanol; it is identical with that described in U.S. Pat. No. 3,312,592.

Replacing said d,p-threo-2-oxiranyl-1,4-benzodioxan by the same amount of the erythro-enantiomer the d,p-erythro-2-(2-tert. butylamino-1-hydroxyethyl)-benzodioxan is obtained, melting at 93°–96°, and the hydrochloride thereof at 155°–157°.

EXAMPLE 6

To the stirred solution of 0.2 molar 3-chloro-perbenzoic acid in 275 ml of methylene chloride is added the solution of 25 g cis-1,4-dichloro-2-butene in 50 ml of methylene chloride. The mixture is stirred at room temperature for 4 days, filtered and the filtrate stirred for 30 minutes with 100 ml of 10% aqueous sodium sulfite. The organic layer is separated, washed with cold 12% aqueous sodium hydroxide and water, dried and evaporated to yield the cis-1,4-dichloro-2,3-epoxybutane boiling at 83°–85°/25 mmHg.

The mixture of 1.7 g thereof, 1.1 g of catechol and 2 ml of isopropanol is heated to 65° and the solution of 0.8 g of sodium hydroxide in 2 ml of water is added dropwise while stirring. The mixture is heated to 85° for 60 minutes, cooled and diluted with benzene. It is washed with water, dried and evaporated, to yield a mixture comprising 48% starting epoxide; 40% desired d,p-threo-2-oxiranyl-benzodioxane and 10% of 2-chloromethyl-3-hydroxymethyl-benzodioxane (by mass-spectroscopy). It is separated by bulb to bulb-distillation and the fraction boiling at 120°/0.2 mmHg collected, to yield said threo-compound.

EXAMPLE 7

To 1.2 lt of refluxing water, 1 ml of 40% aqueous tetrabutylammonium hydroxide, 160 g of 5-chloro-salicylaldehyde and 140 ml of trans-1,4-dichloro-2-butene are added while vigorously stirring, followed by the dropwise addition of the solution of 42 g of sodium hydroxide in 200 ml of water at such a rate that the pH of the mixture is kept between 7 and 8. Thereafter the mixture is refluxed until the pH is about 7, cooled and extracted with methylene chloride. The extract is washed with 5% aqueous sodium hydroxide, dried, evaporated and the residue heated to 30°/0.1 mmHg in order to remove the excess of 1,4-dichloro-2-butene. The residue is taken up in 1 lt of diethyl ether, the solution filtered, the filtrate evaporated and the residue recyrstallized from ethyl acetate, to yield the 5-chloro-2-(4-chloro-trans-2-butenyloxy)-benzaldehyde melting at 62°–63°.

The mixture of 6 g thereof, 20 g of 3-chloroperbenzoic acid and 200 ml of methylene chloride is refluxed for 3 days. It is cooled, filtered and the filtrate washed with 5% aqueous sodium sulfite and 5aqueous sodium bicarbonate, dried and evaporated, to yield the 5-chloro-2-(4-chloro-trans-2,3-epoxybutyloxy)-phenyl formate showing NMR-peaks at 3.3, 3.6, 4.2 and 8.2 ppm.

To the stirred solution of 7 g thereof in 25 ml of methanol 30 ml of 1.75 N aqueous potassium hydroxide are added while cooling and the mixture is stirred for 18 hours at room temperature. It is diluted with water, extracted with diethyl ether, the extract washed with water, dried and evaporated to yield the d,p-erythro-6-chloro-2-oxiranyl-1,4-benzodioxan as an oil, showing NMR-peaks at 2.8, 3.0 and 6.4 ppm and boiling (bulb to bulb) at 130°/0.2 mmHg.

EXAMPLE 8

Replacing the 4-chloro-salicyaldehyde by 152 g of o-vanillin and following the exact procedure given in Example 7, the 2-(4-chloro-trans-2-butenyloxy)-3-methoxybenzaldehyde is obtained, boiling at 165°/0.15 mmHg.

The mixture of 7 g thereof, 21 g of 3-chloroperbenzoic acid and 250 ml of methylene chloride is refluxed for 3 days. It is cooled, filtered and the filtrate washed with 5% aqueous sodium sulfite and 5% aqueous sodium bicarbonate, dried and evaporated, to yield the 2-(4-chloro-trans-2,3-epoxybutyloxy)-3-methoxyphenyl formate, showing NMR-peaks at 3.2, 3.6, 3.9, 4.15 and 8.3 ppm.

To the stirred solution of 8 g thereof in 20 ml of methanol 35 ml of 1.75 N aqueous potassium hydroxide are added while cooling and the mixture is stirred for 18 hours at room temperature. It is concentrated to about half its volume, diluted with 50 ml of water and extracted with diethyl ether. The extract is washed with water, dried and evaporated to yield the d,p-erythro-8-methoxy-2-oxiranyl-1,4-benzodioxan as an oil, showing NMR-peaks at 2.8, 3.1, 3.8 and 6.5 ppm.

EXAMPLE 9

The mixture of 50 g of 2-(4-chloro-trans-2-butenyloxy)-benzaldehyde, 50 g of sodium acetate and 200 ml of acetic acid is refluxed for 2 hours and concentrated. The concentrate is diluted with water, extracted with diethyl ether, the extract washed with water and 5% aqueous sodium bicarbonate, dried and evaporated, to yield the 2-(4-acetoxy-trans-2-butenyloxy)-benzaldehyde.

The mixture of 25 g thereof, 51 g of 3-chloroperbenzoic acid and 500 ml of methylene chloride is refluxed for 3 days. It is cooled, filtered and the filtrate washed with 5% aqueous sodium bicarbonate, dried and evaporated, to yield the 2-(4-acetoxy-trans-2,3-epoxybutyloxy)-phenyl formate.

To the stirred solution of 10 g thereof in 50 ml of methanol is 110 ml of 1.75 N aqueous potassium hydroxide are added while cooling and the mixture is stirred for 18 hours at room temperature and 2 hours at 50°. It is concentrated, the concentrate diluted with water, extracted with methylene chloride, the extract washed with water, dried and evaporated to yield the d,p-erythro-1,4-benzodioxan-2-yl-ethyleneglycol.

To the stirred solution of 5.6 g thereof in 20 ml of pyridine 2.3 ml of methanesulfonyl chloride are added while cooling to keep the temperature at about 20°. Stirring is continued for 10 minutes and the mixture, containing the mono-mesylate, is diluted with 200 ml of diethyl ether. It is stirred at 25° and 10 g of sodium methoxide are slowly added while maintaining said temperature. After stirring for 1 hour the mixture is treated with 200 g of ice, the organic layer separated, washed with 5% hydrochloric acid until neutral, dried and evaporated. The residue is diltilled and the fraction boiling at 120°/0.2 mmHg collected, to yield the d,p-erythro-2-oxiranyl-1,4-benzodioxane, melting at 45°, in substantially higher yield.

EXAMPLE 10

The mixture of 2.5 g of d,p-erythro-2-oxiranyl-1,4-benzodioxan, 1.7 g of 2-(2-oxo-1-benzimidazolyl)-piperidine and 15 ml of isopropanol is refluxed for 4 hours and concentrated to a small volume. The concentrate is diluted with benzene and extracted with 5% hydrochloric acid. The extract is allowed to stand in the cold, the gummy precipitate formed, filtered off and triturated with aqueous ammonnia and chloroform. The organic solution is separated, dried, evaporated and the residue recrystallized from ethyl acetate, whereby the d,p-erythro-2-[2-(4-(2-oxo-1-benzimidazolyl)-piperidino)-1-hydroxyethyl]-1,4-benzodioxan is obtained, melting at 188°-190°; it is identical to that of German Pat. No. 2,400,094.

The analogously obtained d,p-threo-compound melts at 110°-115°.

EXAMPLE 11

5 g of d,p-erythro-2-oxiranyl-1,4-benzodioxan are treated with the solution of 2.4 g of hydrogen bromide in 100 ml of methylene chloride while stirring. The solution formed is allowed to stand overnight at room temperature and evaporated, to yield the d,p-erythro-2-(2-bromo-1-hydroxyethyl)-1,4-benzodioxan showing NMR-peaks between 3.7 and 4.5, as well as at 6.9 ppm.

EXAMPLE 12

The solution of 10.9 g of 5-chloro-2-(4-chloro-trans-2,3-epoxybutyloxy)-phenyl formate in 200 ml of anhydrous diethyl ether is stirred with 43 ml of 1.75 N aqueous potassium hydroxide and 0.2 ml of 40% aqueous tetrabutylammonium hydroxide for 18 hours at room temperature. The organic layer is separated, washed with water, dried and evaporated, to yield the d,p-erythro-6-chloro-2-(2-chloro-1-hydroxyethyl)-1,4-benzodioxan as an oil showing NMR peaks at 3.0, between 3.8 and 4.25 and at 6.7 ppm.

EXAMPLE 13

To 2 lt of refluxing water, 3 ml of 40% aqueous tetrabutylammonium hydroxide, 250 ml of salicylaldehyde and 280 ml of trans-1,4-dichloro-2-butene are added while vigorously stirring, followed by the dropwise addition of the solution of 83 g of sodium hydroxide in 400 ml of water at such a rate that the pH of the mixture is kept between 7 and 8 (ca 25 minutes). Thereafter the mixture is refluxed for about 6 minutes until the pH is about 7, cooled to 20° and the aqueous layer is extracted with diethyl ether. The extract is combined with the organic layer, washed with 5% aqueous sodium hydroxide, dried, evaporated, the residue distilled and the fraction boiling at 141°-147°/0.7 mmHg collected, to yield the 2-(4-chloro-trans-2-butenyloxy)-benzaldehyde.

To the solution of 155.7 g thereof in 3.8 lt of methylene chloride 357 g of 85% 3-chloro-perbenzoic acid are added and the mixture is stirred for one hour and refluxed for 4 days. It is cooled, filtered and the filtrate washed with methylene chloride and saturated aqueous sodium bicarbonate, dried and evaporated below 40°, to yield the 2-(4-chloro-trans-2,3-epoxybutyloxy)-phenyl formate, showing NMR-peaks at 3.2, 3.5, 4.1, 7.0 and 8.2 ppm.

To the solution of 229.4 g thereof in 900 ml of methanol is added dropwise 1.1 lt of 10% aqueous potassium hydroxide while stirring under nitrogen and maintaining the temperature between 8° and 15°. After stirring at said temperature overnight and at room temperature the mixture is decanted from the residue and extracted with diethyl ether. The combined residue and extract is washed with water, dried, evaporated and the residue recrystallized from diethyl ether, to yield the d,l-erythro-2-oxiranyl-1,4-benzodioxan melting at 50°-53°; it is identical with that obtained according to Example 2.

EXAMPLE 14

To 130 lt of ethanol, 12.1 kg of sodium methoxide are added while cooling and stirring, followed by 26.5 kg of salicylaldehyde at 30°. Thereupon 33.3 kg of trans-1,4- dichloro-2-butene are added and the mixture heated to 68° for 4 hours. It is combined with 156 lt of toluene, 187 lt of water and 9.4 kg of 36% hydrochloric acid while keeping the temperature at about 30°. The precipitate formed is filtered off and washed with 16 lt of toluene. The filtrate is separated, the organic layer washed 3 times with 27 lt of water, evaporated, the residue distilled and the fraction boiling at 170°/0.2 mmHg collected, to yield the 2-(4-chloro-trans-2-butenyloxy)-benzaldehyde.

23.0 kg thereof are added to the solution of 63.4 kg of m-chloro-perbenzoic acid in 342 lt of methylene chloride, held at 30°-35°, during 90 minutes. The mixture is refluxed for 48 hours, cooled to room temperature and combined with a sufficient amount of 17% aqueous sodium bisulfite, until the potassium iodide/starch test is negative. The mixture is filtered, the residue washed with 20 lt of methylene chloride, the filtrate separated and the organic layer, containing the 2-(4-chloro-trans-2,3-epoxy-butyloxy)-phenyl formate, collected.

It is diluted with 50 lt of methylene chloride and 125 lt of methanol, and combined with 16.6 kg of 85% technical grade potassium hydroxide in 130 lt of water at 20°-25°. The mixture is stirred for 16 hours at said temperature, the organic layer separated and washed with 50 lt of water multiple times, until the pH of 6.0-7.5 is reached. It is evaporated below 40°/20-50 mmHg, and 93 kg of the crude residue are dissolved in 33 lt of isopropanol at 60°-70°. The solution is cooled to 25°-28°, seeded, gradually cooled to −8° and allowed to stand overnight at said temperature. The precipitate formed is filtered off, washed with 22 lt of isopropanol at −10°, and dried at room temperature and reduced pressure, to yield the d,l-erythro-2-oxiranyl-1,4-benzodioxan melting at 50°-53°; it is identical with that of Examples 2 and 13.

We claim:

1. A process for the stereospecific preparation of a compound of the formula

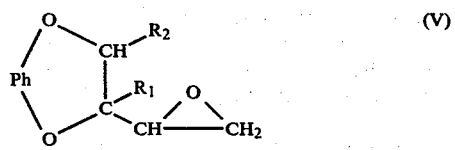

wherein Ph is unsubstituted 1,2-phenylene or 1,2-phenylene substituted by one to three identical or different members selected from lower alkyl, hydroxy, lower alkoxy, lower alkylenedioxy, benzyloxy, lower alkanoyloxy, halogeno, trifluoromethyl or nitro; and $R_1$ and $R_2$ is hydrogen or lower alkyl;

which comprises: (a) reacting a compound of formula II wherein

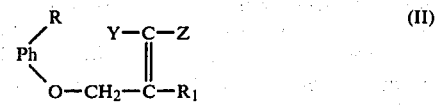

Ph, $R_1$, $R_2$ have meaning defined above, R is CHO, one of Y and Z is $R_2$ and the other is $CH_2X$ wherein X is a halogen atom,
with a compound $R_4$-OOH
wherein $R_4$ is hydrogen, lower alkanoyl, lower haloalkanoyl, HPhCO, HOOC-$C_2H_4$-CO, or HOOC-Ph-CO (b) cyclizing resulting compound III

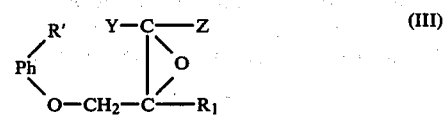

wherein R' is formyloxy and Ph, $R_1$, Y and Z have meanings as defined in (a), with a base, being aqueous alkali, alkaline earth metal hydroxide or a strong quaternary nitrogen base.

2. A process as claimed in claim 1 wherein $R_4$-OOH is m-chloroperbenzoic acid and the base is potassium hydroxide.

3. A process as claimed in claim 1 wherein Ph is 1,2-phenylene unsubstituted or monosubstituted by hydroxy, benzyloxy, fluoro, chloro, bromo, trifluoromethyl, nitro, alkyl, alkoxy or alkanoyloxy with 1-4 carbons, or alkylenedioxy with 1 or 2 carbons; R is CHO; R' is formyloxy; one of Y and Z is $R_2$ and the other is (chloro-, bromo-, or iodo) methyl; and each of $R_1$ and $R_2$ is hydrogen or methyl.

4. A process as claimed in claim 1, wherein Ph is 1,2-phenylene unsubstituted or monosubstituted by methyl, methoxy, methylenedioxy, benzyloxy, formyloxy, acetoxy, fluoro, chloro, trifluoromethyl or nitro; R is CHO; R' is formyloxy; one of Y and Z is hydrogen and the other is chloromethyl, bromomethyl, iodomethyl; and each of $R_1$ and $R_2$ is hydrogen.

5. A process as claimed in claim 1 wherein Ph is 1,2-phenylene, 3-methoxy-1,2-phenylene or 5-chloro-1,2-phenylene; R' is formyloxy; one of Y and Z is hydrogen and the other is chloromethyl, iodomethyl; each of $R_1$ and $R_2$ is hydrogen; and R is CHO.

6. A process as claimed in claim 1 wherein compound of formula V is d,l-erythro-2-oxiranyl-1,4-benzodioxan.

7. A process as claimed in claim 1 wherein compound of formula V is d,l-threo-2-oxiranyl-1,4-benzodioxan.

8. A process as claimed in claim 1 wherein compound of formula V is d,l-erythro-6-chloro-2-oxiranyl-1,4-benzodioxan.

9. A process for the stereospecific preparation of d,l-erythro-1,4-benzodioxan-2-yl-ethyleneglycol which comprises
(a) reacting 2-(4-acetoxy-trans-2-butenyloxy)benzaldehyde with 3-chloroperbenzoic acid; and
(b) treating the resulting 2-(4-acetoxy-trans-2,3-epoxybutyloxy)-phenyl formate with aqueous potassium hydroxide.

* * * * *